A

United States Patent [19]
Li et al.

[11] Patent Number: 5,662,697
[45] Date of Patent: Sep. 2, 1997

[54] TRANSVENOUS INTERNAL CARDIAC DEFIBRILLATION APPARATUS HAVING LEAD AND ELECTRODE PROVIDING EVEN DISTRIBUTION OF ELECTRICAL CHARGE

[75] Inventors: Hong Li, Arcadia, Calif.; John R. Helland, Redmond, Wash.

[73] Assignee: Pacesetter, Inc., Sylmar, Calif.

[21] Appl. No.: 544,334

[22] Filed: Oct. 17, 1995

[51] Int. Cl.⁶ ............................................ A61N 1/39
[52] U.S. Cl. ...................... 607/122; 607/126; 607/5
[58] Field of Search ............................. 607/122, 123, 607/126, 127, 128

[56] References Cited

U.S. PATENT DOCUMENTS

| | | | |
|---|---|---|---|
| 5,063,932 | 11/1991 | Dahl et al. | 128/639 |
| 5,265,623 | 11/1993 | Kroll et al. | 607/122 |
| 5,269,319 | 12/1993 | Schulte et al. | 607/123 |
| 5,271,417 | 12/1993 | Swanson et al. | 607/122 |
| 5,405,375 | 4/1995 | Ayers et al. | 607/122 |
| 5,411,544 | 5/1995 | Mar et al. | 607/122 |
| 5,431,681 | 7/1995 | Helland | 607/119 |

FOREIGN PATENT DOCUMENTS 652597B  6/1992  Australia ................... 607/5

*Primary Examiner*—William E. Kamm
*Assistant Examiner*—Carl H. Layno
*Attorney, Agent, or Firm*—Lisa P. Weinberg

[57] ABSTRACT

A lead for use with an implanted pulse generator which may be a pacemaker or defibrillator or combination thereof. The lead can deliver an electrical charge to cardiovert or defibrillate the ventricles of the heart via a large surface area defibrillation electrode which is passively implanted in the ventricle. The defibrillation electrode is designed to produce a uniform defibrillation charge distribution.

22 Claims, 2 Drawing Sheets

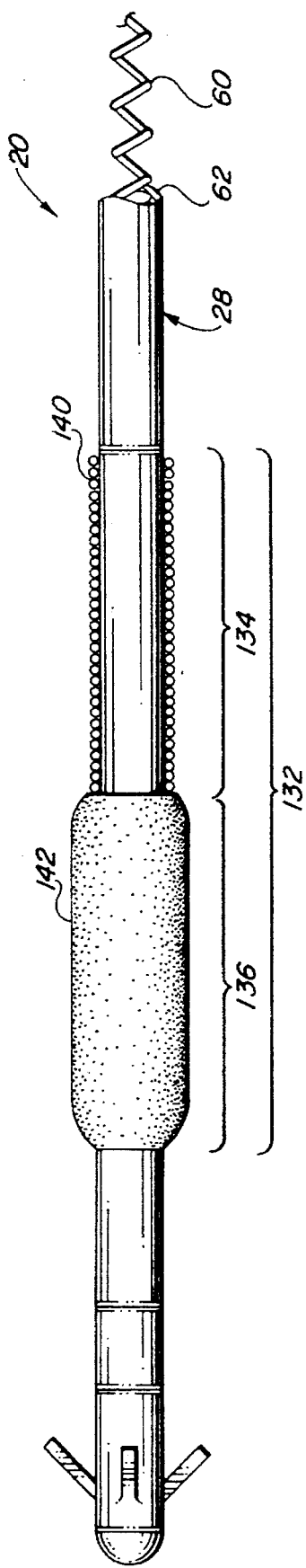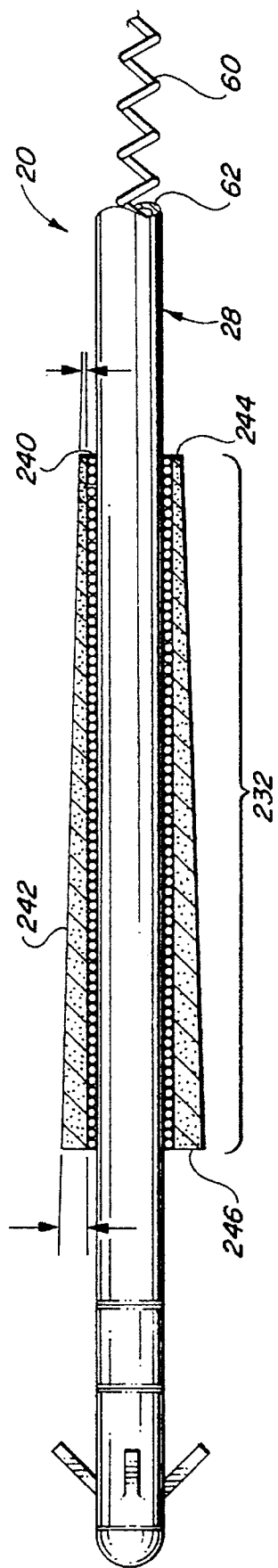

TRANSVENOUS INTERNAL CARDIAC DEFIBRILLATION APPARATUS HAVING LEAD AND ELECTRODE PROVIDING EVEN DISTRIBUTION OF ELECTRICAL CHARGE

FIELD OF THE INVENTION

The present invention relates generally to medical electronic devices and, more particularly, to implantable devices for pacing, cardioverting, or defibrillating a heart. Specifically, the present invention is directed to a transvenous implanted lead which is operably connected to an implanted pacemaker and/or defibrillator. The lead is designed to be placed into the ventricle and includes a defibrillation electrode providing even distribution of electrical charge to cardiovert or defibrillate the heart. The lead also preferably includes a pacing electrode which can sense electrical activity in the heart.

BACKGROUND OF THE INVENTION

A number of types of implantable devices are in use to monitor and control the electrical activity of the heart. These devices include an implanted pacemaker and/or defibrillator connected to one or more transvenous leads having one or more electrodes. These devices can apply electrical pacing or defibrillation charges directly to the myocardial tissue of the heart. Generally, the electrodes can both sense the electrical activity of the heart and deliver an electrical stimulus provided by the pacemaker when required.

Combination pacing and defibrillation systems connected to a combination lead having both pacing and defibrillation electrodes implanted into the ventricle have also been disclosed in the art. For these types of combination leads, the pacing electrode is located at the distal tip of the combination lead, with the defibrillation electrode generally spaced proximally from the distal tip yet sized to be positioned within the ventricle. The defibrillation electrode generally has a large surface area, as compared to the pacing electrode, because the defibrillation electrode delivers a substantially greater electrical stimulation charge over a greater mass of cardiac tissue.

It is preferable to have the large defibrillation charge delivered by the defibrillation electrode distributed over a substantial surface area of the heart, to avoid damaging the tissue by exposure to a high electrical charge over a limited surface area. However, the design of existing defibrillation electrodes of combination leads inherently provides an uneven charge distribution over its entire surface area, due to the electrical resistance of the electrode itself. As a result, damage to the heart tissue or to the blood may occur when a defibrillation pulse is applied. Moreover, inefficient distribution of the defibrillation pulse may result in unnecessarily high current having to be used to achieve cardioversion or defibrillation.

Accordingly, it would be beneficial to provide a lead for a cardioversion or defibrillation system which features an improved design for the defibrillation electrode capable of producing a more uniform charge distribution.

SUMMARY OF THE INVENTION

The present invention details a lead having a defibrillation electrode for an implantable defibrillation system including an implanted pulse generator. Preferably, the defibrillation electrode is part of a lead which also includes a pacing electrode. The lead can deliver a variety of electrical charges to pace, cardiovert, or defibrillate the ventricles of the heart.

The lead allows cardioversion and/or defibrillation stimuli to be provided by a large surface area defibrillation electrode located proximally to a pacing electrode positioned at the distal tip of the lead. By this configuration, the defibrillation electrode is positioned within the ventricle following implant. The defibrillation electrode is designed to provide a more uniform distribution of electrical charge to the myocardial tissue of the ventricle.

In accordance with the present invention, three embodiments of the defibrillation electrode are depicted. Generally, all three embodiments provide for more uniform charge distribution. In the first embodiment, the defibrillation electrode includes two or more exposed electrode segments separated by an insulation material. The electrode segments may be part of a single long electrode having one or more insulation rings impregnating the exposed surface of the defibrillation electrode. Alternatively, the defibrillation electrode may be a single long electrode having a variable porosity or thickness coating of electrically conductive material applied to the exposed surfaces of the defibrillation electrode. Another embodiment depicts a defibrillation electrode wherein a portion includes a porous coating of electrically conductive material which enhances electrical continuity between the coated surface of the defibrillation electrode and the surrounding body fluids.

For all of the embodiments, the design of the defibrillation electrode of the present invention is equally applicable to a lead providing only defibrillation capability which does not have a pacing electrode.

BRIEF DESCRIPTION OF THE DRAWINGS

FIG. 3 depicts the distal end Of a lead including a first alternative embodiment of the defibrillation electrode according to the present invention.

FIG. 4 depicts the distal end of a lead including a second alternative embodiment of the defibrillation electrode according to the present invention.

DETAILED DESCRIPTION OF THE PREFERRED EMBODIMENT

Figure 1:
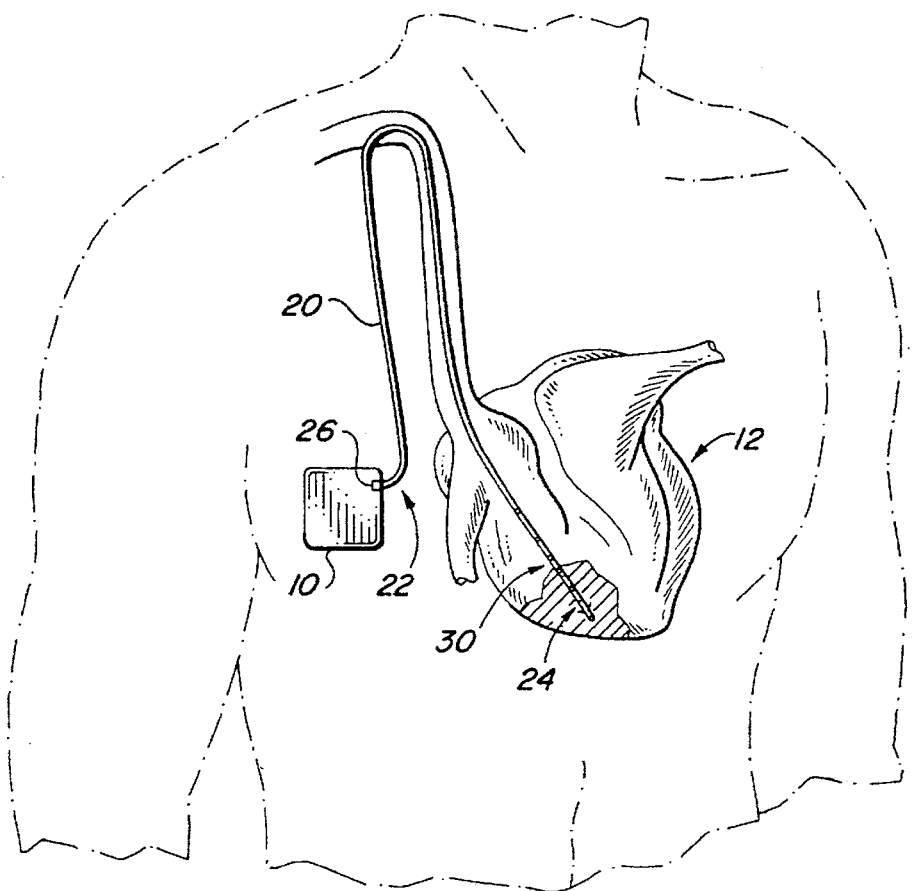
FIG. 1. depicts an implanted pulse generator interconnected via a lead including a defibrillation electrode transvenously implanted into a heart.

FIG. 1 depicts an implanted signal processing and pulse generating means such as a pulse generator 10 interconnected to a heart 12 via a lead 20. The lead 20 is transvenously inserted and extends to the right ventricle of the heart 12. The lead 20 includes a proximal end 22 and a distal end 24. At the proximal end 22, a connector assembly 26 accommodates interconnection with the pulse generator 10. A lead body 28, having one or more electrical conductors (not shown) extends from the proximal end 22 to the distal end 24 of the lead 20.

An electrode assembly 30 is located at the distal end 24 of the lead 20. Preferred embodiments of the electrode assembly 30 are depicted in the enlarged views of the distal end 24 of the lead 20 depicted in FIGS. 2–4. For the following discussion, the elements which are identical in all of the FIGS. 2–4 will be similarly numbered, and discussed only in reference to FIG. 2.

Figure 2:
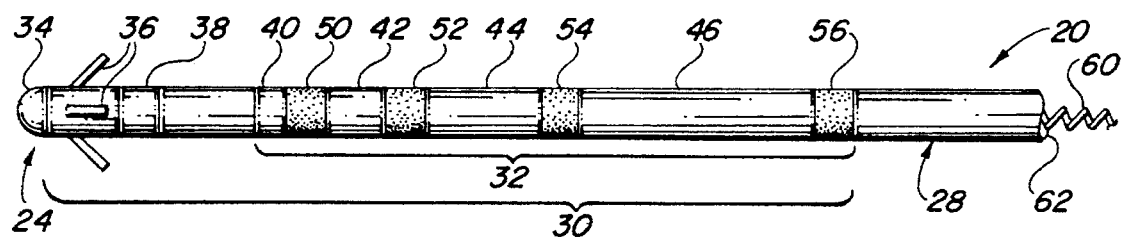
FIG. 2 depicts the distal end of a lead including the defibrillation electrode according to the present invention.

In FIG. 2 the distal end 24 of lead 20 and specifically the electrode assembly 30 are depicted in greater detail. The electrode assembly 30 includes a defibrillation electrode 32 which is shown interconnected to a distal end of the lead body 28. The defibrillation electrode 32 is designed to deliver defibrillation or cardioversion stimuli.

The electrode assembly 30 may also include a pacing electrode 34 located at the distal end 24 of the lead 20. The pacing electrode 34 is used with the pulse generator 10 to deliver a pacing electrical pulse to the heart, and also to sense cardiac electrical activity, in either a unipolar or bipolar arrangement. The lead 20 may also include a plurality of tines 36 positioned near the distal end 24, to help secure the positioning of the pacing electrode 34 after implant.

The electrode assembly 30 may further include a ring sensor 38 positioned between the pacing electrode 34 and the defibrillation electrode 30. The ring sensor 38 may be used in a bipolar arrangement for pacing, with the pacing electrode 34 acting as the cathode and the ring sensor 38 acting as an electrical anode. Alternatively, the ring sensor 38 may be a sensor, operative with, or independently of, the pacing electrode 34. The ring sensor 38 is preferably locate between the defibrillation electrode 32 and the pacing electrode 34. The ring sensor 38 is preferably spaced from the defibrillation electrode a distance of between about one (1) and three (3) centimeters. Following implant of the lead 20, the defibrillation electrode 32 will be positioned within the ventricle, as will the ring sensor 38.

The defibrillation electrode 32 illustrated in FIG. 2 includes a first segment 40 closest to the distal end 24 of the lead 20, and proceeding proximally, a second segment 42, a third segment 44 and a fourth segment 46, each spaced from respective adjacent segments by insulators 50, 52 and 54. An additional insulator 56 may be positioned at the proximal end of the fourth segment 46. The respective segments 40, 42, 44 and 46 are all part of the defibrillation electrode 32 and may either be continuous under, the insulators 50, 52 and 54, or they are discreet elements.

All of the segments 40, 42, 44 and 46 forming the defibrillation electrode 32 are interconnected to a single defibrillation conductor 60 extending through the lead body 28. The defibrillation conductor 60 is encased in an insulation material 62 preferably formed from a biocompatible plastic or elastomeric material such as, for example, silicone rubber. The defibrillation conductor 60 is preferably a helically wound coil of multifilar conductor wires which have a core of silver (not shown).

Figure 5:
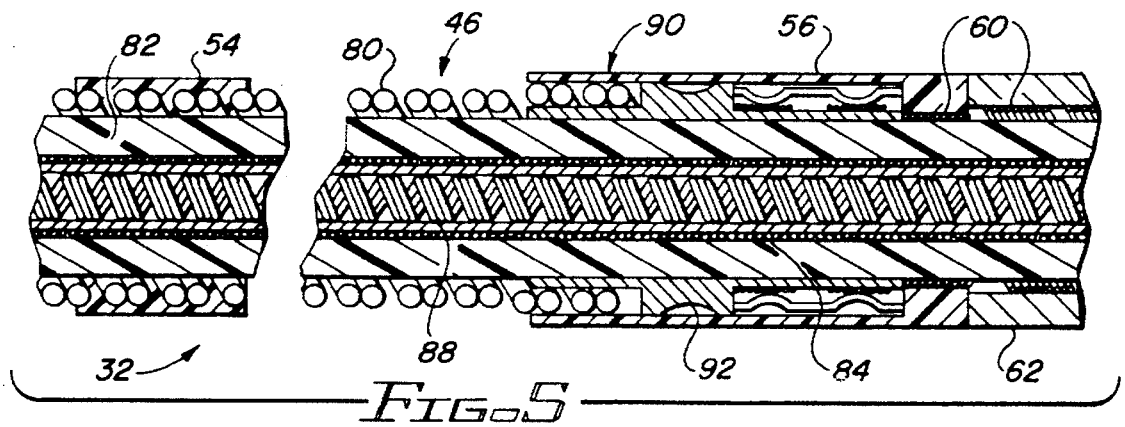
FIG. 5 depicts a cross sectional view through a portion of the defibrillation electrode of the lead according to the present invention.

The defibrillation conductor 60 is preferably interconnected to a proximal end of the fourth segment 46 of the defibrillation electrode 32 as detailed in FIG. 5. The electrical resistance of the conductive material from which the defibrillation electrode 32 is constructed, would normally result in a decrease in the charge density per unit length with increasing distance from the connection to the defibrillation conductor 60 at the proximal end of the fourth segment 46. Dividing the defibrillation electrode 32 into the respective segments 40, 42, 44 and 46 by the use of the insulators 50, 52 and 54 tends to balance the electrical charge distribution over the entire length of the defibrillation electrode 32. More specifically, upon application of a defibrillation pulse, the current density can be made more uniform along the entire length of the defibrillation electrode 32. The uniform distribution of current density results in a more efficient cardioversion or defibrillation shock, and thus lower defibrillation thresholds.

It may also be preferable to have the size of the respective segments 40, 42, 44 and 46 vary, as depicted in FIG. 2. Thus, since all of the segments have the same circumference, the fourth segment 46 is preferably the largest in axial length, and the axial length decreases as the respective segments are spaced distally from the fourth segment 46 so that the first segment 40 has the smallest axial length. For example, if the first segment 40 has a unit axial length of one, the second segment 42 may have a unit axial length of about two, the third segment 44 may have a unit axial length of between three and five, and the fourth segment 46 may have a unit axial length of between about five and ten. The axial length of the entire defibrillation electrode 32 is preferably in the range of between about two to eight centimeters.

The insulators 50, 52 and 54 may all have about the same axial length as illustrated in FIG. 2, which is approximately equal to the axial length of the first segment 40. Alternatively, the respective axial lengths of the insulators 50, 52 and 54 may vary, although not as dramatically as the variations in the axial lengths of the segments 40, 42, 44 and 46.

FIG. 3 depicts a first alternative embodiment for a defibrillation electrode 132 for incorporation into the lead 20 of the present invention. The defibrillation electrode 132 as illustrated in FIG. 3 includes a proximal segment 134 and a distal segment 136. As in FIG. 2, a proximal end of the defibrillation electrode 132 is interconnected to the defibrillation conductor 60 extending through the lead body 28.

The proximal segment 134 of the defibrillation electrode is simply an exposed conductive element such as a coil 140 formed from a platinum-iridium wire, or similar electrically conductive wire or wire mesh. The distal segment 136 is a continuation of the coil 140, however, the distal segment also includes a porous coating 142 to enhance electrical coupling to the surrounding fluids. The porous coating 142 is an electrically conductive material such as titanium-nitride or platinum black. The porosity and the thickness of the porous coating 142 can be varied, thereby increasing the surface area of the distal segment 136 and increasing the net current delivered by the distal segment 136, so that it is approximately equal per unit length to that of the proximal segment 134.

FIG. 4 depicts a second alternative embodiment for a defibrillation electrode 232 for incorporation into the lead 20 of the present invention. The defibrillation electrode 232 as illustrated in FIG. 4 includes a coil 240 formed from a platinum-iridium wire, or similar electrically conductive wire or wire mesh. The coil 240 is coated with a porous coating 242 of electrically conductive material to enhance electrical coupling to the surrounding fluids. The porous coating 242 may be a material such as titanium-nitride or platinum black. The porous coating 242 is applied so that its thickness increases from a proximal end 244 of the defibrillation electrode 232 to a distal end 246 of the defibrillation electrode 232. For example, at the proximal end 244 of the defibrillation electrode 232 the thickness of the porous coating 242 may be only about one micron, while at the distal end 246 of the defibrillation electrode 232 the thickness of the porous coating 242 may be about sixteen to twenty microns. Alternatively, the porosity of the porous coating 242 can be varied, thereby increasing the surface area at the distal end 246 and increasing the net current per unit length delivered by the distal end 246 so that it is approximately equal to that of the proximal end 244.

By varying the thickness and/or the porosity of the porous coating 242 from the proximal end 244 to the distal end 246, the surface area per unit length increases toward the distal end 246. As a result, the distal end 246 is more efficient at delivering and distributing the defibrillation pulse, as the pulse can be distributed over a greater surface area. By this construction, the net current output per unit length becomes relatively uniform along the entire length of the defibrillation electrode 232.

FIG. 5 depicts a partial cross sectional view through an axial portion of the defibrillation electrode 32 of FIG. 2. The general design of the defibrillation electrode 32 and the pass through conductors for the pacing electrode 34 and ring sensor 38, as shown in FIG. 5, may also be used for the defibrillation electrodes 132 and 232 of FIGS. 3 and 4.

The defibrillation electrode 32 is preferably a coil 80 wrapped about an insulation sleeve 82, through which pass a pacing/sensing conductor 84 formed about insulation material 86 which in turn encases a pacing conductor 88. Preferably, the coil 80 of the defibrillation electrode 32 is formed from a platinum-iridium wire.

The coil 80 may be electrically connected to the defibrillation conductor 60 at the proximal end 90 of the coil 80, via a connector element 92. Alternatively, it could connect at the distal end of the lead. The connector element 92 preferably interconnects the coil 80 of the defibrillation electrode 32, to the insulation material 62 encasing the defibrillation conductor 60, as well as to the insulation sleeve 82, about which the coil 80 is wrapped. The connector element 92 includes an axial bore through which the remainder of the components pass prior to entering the central portion of the coil 80.

The pacing electrode 34 may be simply a passive fixation electrode as shown or an active fixation corkscrew or helix electrode both of which are well known in the art. The pacing electrode 34 is affixed to the pacing conductor 88 extending axially through the defibrillation electrode 32 and the lead body 28 to the connector assembly at the proximal end of the lead body 28.

The defibrillation electrode 32 may include a coating deposited on the coil 80, the material for the coating being platinum black, carbon, titanium, or titanium nitride. The defibrillation electrode 32 preferably has a total surface area in the range of between about two and ten square centimeters, with a preferred size of between four and six square centimeters.

It should be evident from the foregoing description that the present invention provides many advantages over leads and pacing or defibrillating systems of the prior art. Although preferred embodiments are specifically illustrated and described herein, it will be appreciated that many modifications and variations of the present invention are possible in light of the above teaching to those skilled in the art. It is preferred, therefore, that the present invention be limited not by the specific disclosure herein, but only by the appended claims.

What is claimed is:

1. An apparatus for ventricular cardioverting or defibrillation of a heart comprising:

an implantable pulse generator;

a lead having a proximal end and a distal end;

a connector assembly attached to the proximal end of said lead, said connector assembly allowing connection of said lead to said pulse generator;

an electrode assembly located at the distal end of said lead, said electrode assembly including a defibrillation electrode positioned proximally from the distal end of said lead;

a defibrillation conductor extending from said connector assembly at the proximal end of said lead to the defibrillation electrode at the distal end of said lead; and means for evenly distributing electrical charge emitted by said defibrillation electrode comprising at least one insulator dividing said defibrillation electrode into at least two electrically interconnected segments, each segment having an axial length, and wherein the respective axial lengths of said electrically interconnected segments decreases from a proximal end of said defibrillation electrode to a distal end of said defibrillation electrode.

2. The apparatus, according to claim 1, wherein said means for evenly distributing electrical charge includes a porous coating of electrically conductive material covering at least a portion of said defibrillation electrode.

3. The apparatus, according to claim 2, wherein said porous coating comprises a material selected from the group consisting of titanium-nitride and platinum black.

4. The apparatus, according to claim 2, wherein said porous coating has a thickness which increases from a proximal end of said defibrillation electrode to a distal end of said defibrillation electrode.

5. The apparatus, according to claim 4, wherein the thickness of said porous coating at the proximal end of said defibrillation electrode is about one micron, and the thickness of said porous coating increases to between about sixteen to twenty microns at the distal end of said defibrillation electrode.

6. The apparatus, according to claim 2, wherein said porous coating has a porosity which increases from a proximal end of said defibrillation electrode to a distal end of said defibrillation electrode.

7. The apparatus, according to claim 6, wherein said porous coating comprises a material selected from the group consisting of titanium-nitride and platinum black.

8. The apparatus of claim 1, wherein said lead further includes a pacing electrode at a distal tip of said electrode assembly.

9. The apparatus of claim 8, wherein said lead further includes a ring sensor positioned proximally from said pacing electrode.

10. The apparatus of claim 8, wherein said lead further includes a ring sensor positioned distally from said defibrillation electrode.

11. The apparatus of claim 1, wherein said lead further comprises:

a pacing electrode at a distal tip of said electrode assembly;

a pacing conductor extending from said connector assembly at the proximal end of said lead to said pacing electrode at the distal tip of said electrode assembly;

a ring sensor positioned proximally from said pacing electrode; and a sensor conductor extending from said connector assembly at the proximal end of said lead to said ring sensor.

12. The apparatus, according to claim 11, wherein the lead further comprises:

a lead body including said defibrillation conductor, said pacing conductor and said sensor conductor contained within an insulator.

13. The apparatus of claim 1, wherein said defibrillation electrode has a total geometric surface area in the range of between about two and ten square centimeters.

14. A lead adapted for connection to an implantable pulse generator, said lead comprising:

a lead body having a proximal end and a distal end;

a connector assembly attached to the proximal end of said lead body;

a defibrillation electrode positioned near the distal end of said lead body, said defibrillation electrode configured to be passively implanted in the ventricle of a heart;

a defibrillation conductor extending through said lead body from said connector assembly at the proximal end to said defibrillation electrode at the distal end of said lead body; and means for evenly distributing electrical charge emitted by said defibrillation electrode, comprising at least one insulator covering an external portion of said defibrillation electrode to divide said defibrillation electrode into at least two electrically interconnected segments, each segment having an axial length, and the respective axial lengths of said at least two electrically interconnected segments decreasing from a proximal end of said defibrillation electrode to a distal end of said defibrillation electrode.

15. The lead, according to claim 14, wherein said means for evenly distributing electrical charge includes a porous coating of electrically conductive material coating at least a portion of said defibrillation electrode.

16. The lead, according to claim 15, wherein said porous coating comprises a material selected from the group consisting of titanium-nitride and platinum black.

17. The lead, according to claim 15, wherein said porous coating has a thickness which increases from a proximal end of said defibrillation electrode to a distal end of said defibrillation electrode.

18. The lead, according to claim 17, wherein the thickness of said porous coating at the proximal end of the defibrillation electrode is about one micron, and the thickness of said porous coating increases to between about sixteen to twenty microns at the distal end of said defibrillation electrode.

19. The lead, according to claim 15, wherein said porous coating has a porosity which increases from a proximal end of said defibrillation electrode to a distal end of said defibrillation electrode.

20. The lead, according to claim 19, wherein said porous coating comprises a material selected from the group consisting of titanium-nitride and platinum black.

21. The lead, according to claim 14, wherein said lead further comprises:

a pacing electrode at a distal tip of said electrode assembly;

a pacing conductor extending from said connector assembly at the proximal end of said lead to said pacing electrode at the distal tip of said electrode assembly;

a ring sensor positioned proximally from said pacing electrode; and a sensor conductor extending from said connector assembly at the proximal end of said lead to said ring sensor.

22. The lead of claim 14 wherein said defibrillation electrode comprises a coil formed from a platinum-iridium wire.

\* \* \* \* \*